(12) United States Patent  (10) Patent No.: US 7,666,679 B2
Herzhaft et al.  (45) Date of Patent: Feb. 23, 2010

(54) METHOD AND DEVICE FOR ANALYZING THE $CO_2$ CONTAINED IN A DRILLING FLUID

(75) Inventors: Benjamin Herzhaft, Suresnes (FR); Marcel Ropars, Palaiseau (FR); Thierry Huard, Montrouge (FR); Laurent Neau, Rueil Malmaison (FR)

(73) Assignee: Institut Francais du Petrole (FR)

( * ) Notice: Subject to any disclaimer, the term of this patent is extended or adjusted under 35 U.S.C. 154(b) by 1188 days.

(21) Appl. No.: 10/797,004

(22) Filed: Mar. 11, 2004

(65) Prior Publication Data

US 2004/0203160 A1  Oct. 14, 2004

(30) Foreign Application Priority Data

Mar. 11, 2003  (FR) .................................. 03 03073

(51) Int. Cl.
*G01N 33/24*  (2006.01)
(52) U.S. Cl. ....................... 436/32; 422/68.1
(58) Field of Classification Search ................ 436/30, 436/133, 145, 25; 422/68.1, 12; 73/1.02, 73/152.21; 166/264, 402; 175/59; 23/306
See application file for complete search history.

(56) References Cited

U.S. PATENT DOCUMENTS

| | | | |
|---|---|---|---|
| 3,685,345 A * | 8/1972 | Wise | 73/19.1 |
| 4,019,862 A * | 4/1977 | Dahms | 436/68 |
| 4,214,628 A * | 7/1980 | Botts | 166/90.1 |
| 4,299,794 A * | 11/1981 | Kelley et al. | 422/82.13 |
| 4,397,957 A * | 8/1983 | Allison | 436/133 |
| 4,661,459 A * | 4/1987 | Hirtz | 436/25 |
| 4,851,195 A * | 7/1989 | Matthews et al. | 422/82.07 |
| 4,904,603 A * | 2/1990 | Jones et al. | 436/25 |
| 4,938,060 A * | 7/1990 | Sizer et al. | 73/152.58 |
| 4,994,117 A * | 2/1991 | Fehder | 436/133 |
| 5,272,088 A * | 12/1993 | Morlotti | 436/68 |
| 5,319,966 A | 6/1994 | Jackson | |
| 5,858,791 A * | 1/1999 | Lemaire | 436/25 |
| 5,909,779 A * | 6/1999 | Patel et al. | 175/50 |
| 5,992,213 A | 11/1999 | Tartre | |
| 6,289,714 B1 | 9/2001 | Tartre | |

FOREIGN PATENT DOCUMENTS

JP  62 083647  4/1987

* cited by examiner

*Primary Examiner*—Jennifer K Michener
*Assistant Examiner*—Imran Akram
(74) *Attorney, Agent, or Firm*—Antonelli, Terry, Stout & Kraus, LLP.

(57) ABSTRACT

A method for estimating the quantity of $CO_2$ present in a geologic formation and a device for implementing the method include the steps of penetrating the formation by a well drilled from the surface contacting formation with a fluid that travels from the formation to the surface sampling a given quantity of return fluid at the surface and transferring it to a cell, ensuring the pH of the quantity of fluid, adding a given quantity of product acidifying the fluid to adjust the pH to a value of less than 4, and measuring the $CO_2$ level of the gas in the cell after the acidification step.

12 Claims, 2 Drawing Sheets

METHOD AND DEVICE FOR ANALYZING THE CO₂ CONTAINED IN A DRILLING FLUID

The present invention relates to the field of geological surveillance of an underground reservoir, or of geological formations traversed by a borehole. The surveillance consists in particular of continuous or near-continuous analysis of the $CO_2$ level of the fluid in contact with the reservoir or formations, namely the drilling fluid or, more generally, a well fluid.

A precise, continuous analysis of the $CO_2$ present in the drilling mud or fluids is a considerable advantage for oil operators. This is because good detection of the amount of $CO_2$ in the reservoir during drilling is extremely important both for financial and for safety reasons. Too much $CO_2$ in the reservoir effluent can generate additional costs when the well is brought into production, or even cause well operation to be abandoned. At the present time, the steps taken after the fact on samples of reservoir rock taken from the well do not offer sufficient safety, and another technique providing the desired information quickly during drilling appears to be essential.

Gas analysis devices contained in the drilling fluid are known, but none of them enable the $CO_2$ to be precisely measured, as according to the present invention.

Thus, the present invention relates to a method for estimating the quantity of $CO_2$ present in a geologic formation comprising the following steps:
  said formation is penetrated by a well drilled from the surface,
  said formation is contacted with a drilling fluid having a pH greater than 8 that travels from the formation to the surface,
  a given quantity of return fluid is sampled at the surface and transferred to a cell,
  the pH of said quantity of fluid in the cell is measured,
  a given quantity of acidifying product is added to said fluid to adjust the pH to a value of less than 4,
  the $CO_2$ level of the gas contained in the cell is measured after the acidification step,
  the quantity of $CO_2$ contained in the geologic formation is calculated from the previous $CO_2$ measurement.

According to the invention, the quantity of carbonate supplied by the geologic formation and/or by the additives in the formulation of said fluid can be taken into account.

The pH of the quantity of fluid can be adjusted to approximately 2.

The gas can be transferred by an inert gas scavenging the internal space of the cell.

The additives in the mud formulation can be taken account by running the $CO_2$ measurement method on a given volume of initial fluid, i.e. before contact with the formation.

The sampling rate can be determined according to the fluid travel rate.

The invention also relates to a device for estimating the quantity of $CO_2$ present in a geologic formation traversed by a well in which a fluid, for example a drilling fluid, travels between said formation and the wellhead at the surface. The device comprises means for sampling a given quantity of return fluid at the wellhead, a cell serving as a receptacle for said quantity of fluid, means for measuring the pH in said cell, means for inert-gas scavenging of the internal space of the cell, means for injecting an acidifying product into said cell, and means for measuring the quantity of $CO_2$ contained in the internal space of the cell.

Adjusting means can control the acid injection means according to the pH measurement.

The means for measuring the quantity of $CO_2$ can comprise an infrared cell or a thermal conductivity measuring cell.

Control means can carry out the following steps, at a rate determined by the fluid flowrate:
  Sampling of a quantity of fluid;
  Measurement of pH;
  Injection of a quantity of acid;
  Scavenging the cell space;
  Measurement of $CO_2$;
  emptying the cell.

The device can include means for measuring the internal pressure of said cell.

The device can include means for regulating the temperature of said cell.

The present invention will be better understood and its advantages will emerge more clearly from reading the following description of non-limiting embodiment examples illustrated by the attached figures.

The present invention provides access to measurements of the entire quantity of the $CO_2$ present in a geologic formation. These measurements are made on the carrier fluid between the geologic formation and the surface of the ground. The drilling fluid travels upward in the drilled well, entraining the $CO_2$ from the bottom to the surface. By degasifying the drilling fluid on its return to the surface, whether naturally or artificially, one can measure the degassed $CO_2$, but the interaction of this fluid with the $CO_2$ considerably distorts estimates of the amount of the $CO_2$ in place in the geologic formation.

This is clearly seen by looking at the behavior of $CO_2$ gas mixtures in the presence of drilling muds.

Drilling muds (water-based or oil-based fluid) are made at the surface, with a pH greater than 8. The mud formulation almost invariably includes large amounts of salt (NaCl, $CaCl_2$) and possibly carbonates ($CaCO_3$) to adjust the density of the fluid. The following table shows an example of a typical oil-based drilling fluid formulation:

| COMPONENT | WEIGHT (g) |
|---|---|
| Oil | 470 |
| Filtrate reducer | 6 |
| Emulsifier | 18 |
| Wetting agent | 2.9 |
| Lime | 20 |
| Clay | 15 |
| Viscosifier | 4 |
| Brine | 322 |
| $CaCO_3$ (weighting material) | 260 |

As shown in the table above, the formulation of an oil-based mud is a complex and highly saline aqueous emulsified mixture. This salinity has an effect on the solubility of the gases, particularly $CO_2$.

A drilling mud in contact with gaseous $CO_2$ establishes a number of chemical equilibria.

First, the $CO_2$ becomes partially dissolved in the mud according to Henry's law, and an equilibrium is established between the gaseous $CO_2$ and the dissolved $CO_2$ according to the formula: $[CO_{2aqueous}] = K \times PCO_2$, K being Henry's constant (depending on the mud formulation) and $PCO_2$, the $CO_2$ partial pressure in the top gas phase that is in contact with the mud.

Also, because of the pH of the mud, an equilibrium is established between the aqueous $CO_2$, $HCO_3^-$, and $CO_3^{2-}$ species according to the following formulae:

Aqueous $CO_2 + H_2O \leftrightarrow HCO_3^- + H^+$ pKa=6.4

$HCO_3^- \leftrightarrow CO_3^{2-} + H^+$ pKa=10.3

Figure 1:
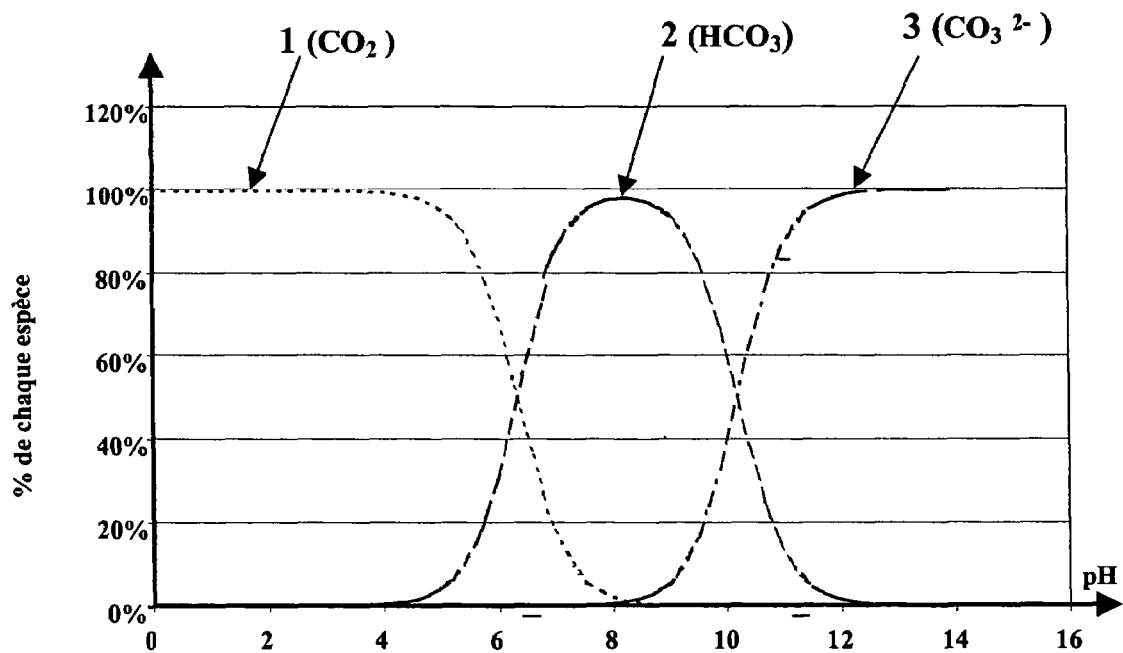
FIG. 1 shows the distribution of carbon-containing species as a function of pH.

FIG. 1 shows the percentages of the various $CO_2$-based compounds as a function of pH. Curves 1, 2, and 3 represent the compounds $CO_2$, $HCO_3^-$, and $CO_3^{2-}$, respectively.

In addition to the physical solubility properties of $CO_2$, the chemical properties are conferred on the solution by the calcium carbonate according to the following reactions:
Solubility of carbonates: $\downarrow CaCO_3 \leftrightarrow Ca^{2+} + CO_3^{2-}$ pKs=8.3
Reaction of carbonates with dissolved $CO_2$ according to:

$CO_{2aqueous} + H_2O + CaCO_3 \leftrightarrow Ca(HCO_3)_2$

The latter reaction has a strong rightward displacement for high pH values and will continue as long as calcium carbonate is available in the formulation. Because of the high pH values of certain drilling muds and the present of $Ca^{2+}$ ions, the equilibrium tends to shift to formation of carbonates and hydrogen carbonates $Ca(HCO_3)_2$.

Hence a drilling mud tends to function like a "$CO_2$ pump."

Figure 2:
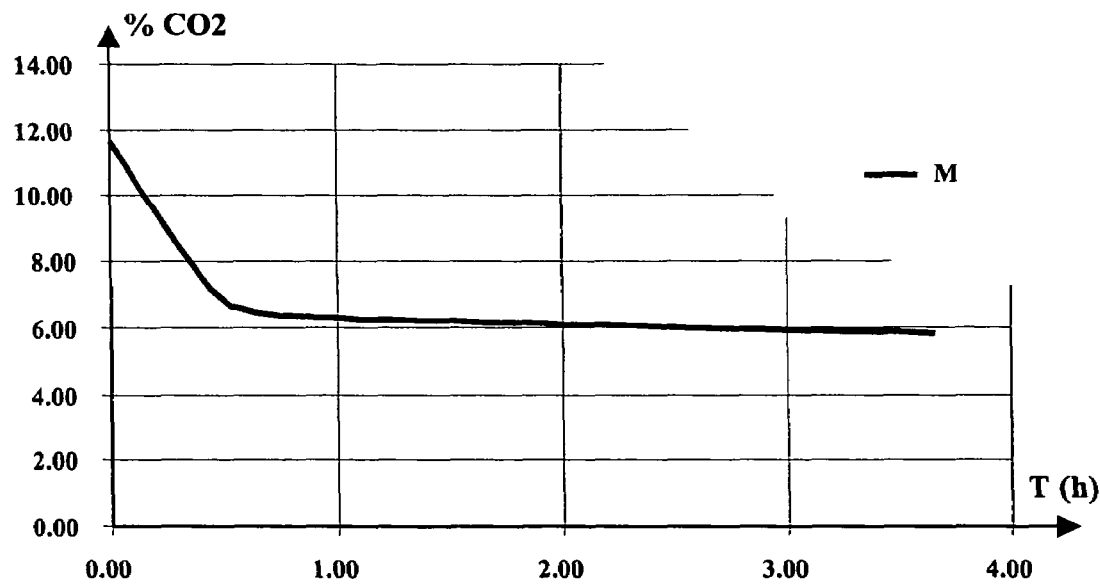
FIG. 2 shows the interaction of a water-based drilling fluid and a gas composition containing $CO_2$.

FIG. 2 shows the change in composition of a top gas phase as a function of time T (in hours), initially at 13% $CO_2$ in air, when it contacts a water-base mud with pH=8.5, with the formulation given below:

| COMPONENT | WEIGHT (g) |
|---|---|
| Water | 1000 |
| Clay | 30 |
| Xanthane | 2.5 |
| CMC | 3 |
| Viscosifier | 5 |
| NaCl | 30 |
| Baryte (weighting material) | 210 |

It can be seen that an equilibrium is established very quickly (less than one hour) after conversion of $CO_2$ into $HCO^{3-}$.

Figure 3:
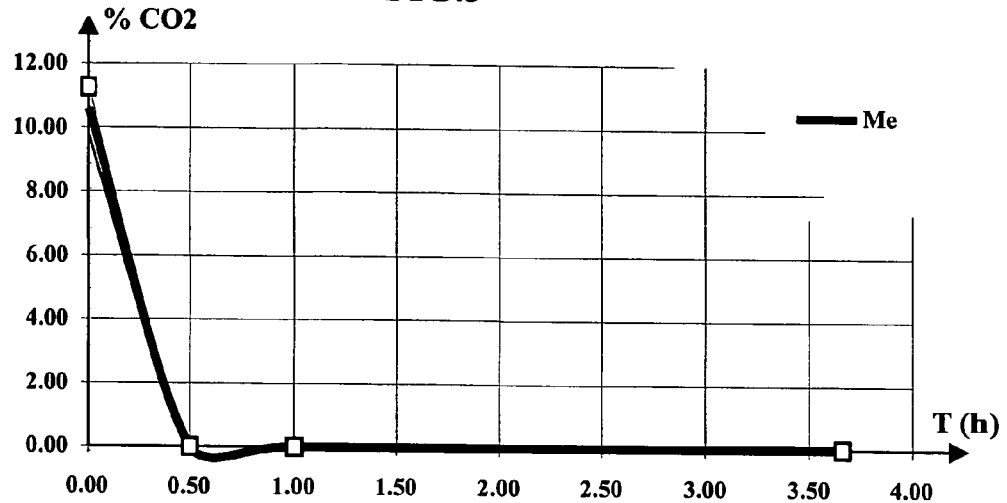
FIG. 3 shows the interaction of an oil-based drilling fluid and a gaseous composition containing $CO_2$.

In the case of an oil-base mud with pH=10.5 (FIG. 3), under the same top gas phase conditions, all the $CO_2$ has been consumed by the mud. No solubility equilibrium appears, showing that $CO_2$ is present in the form of carbonates or hydrogen carbonates dissolved in the mud.

To measure the $CO_2$ carried by the drilling mud, one must thus determine the proportions of the carbonate and hydrogen carbonate species present in the mud, particularly by shifting the chemical equilibriums.

For this purpose, according to the invention, strong acidification of the medium enables the various species to be converted into gaseous $CO_2$. The $CO_2$ release can be effected by strongly acidifying the solution by injecting concentrated acid until a pH of less than 4 and preferably approximately 2 is reached.

At a pH of 2, all the carbonate species will have been converted into gaseous $CO_2$, the level of which can be measured with an infrared sensor or by thermal conductivity. The rise in pressure in the measuring cell can also be an indirect measurement of the amount of $CO_2$ released.

Figure 4:
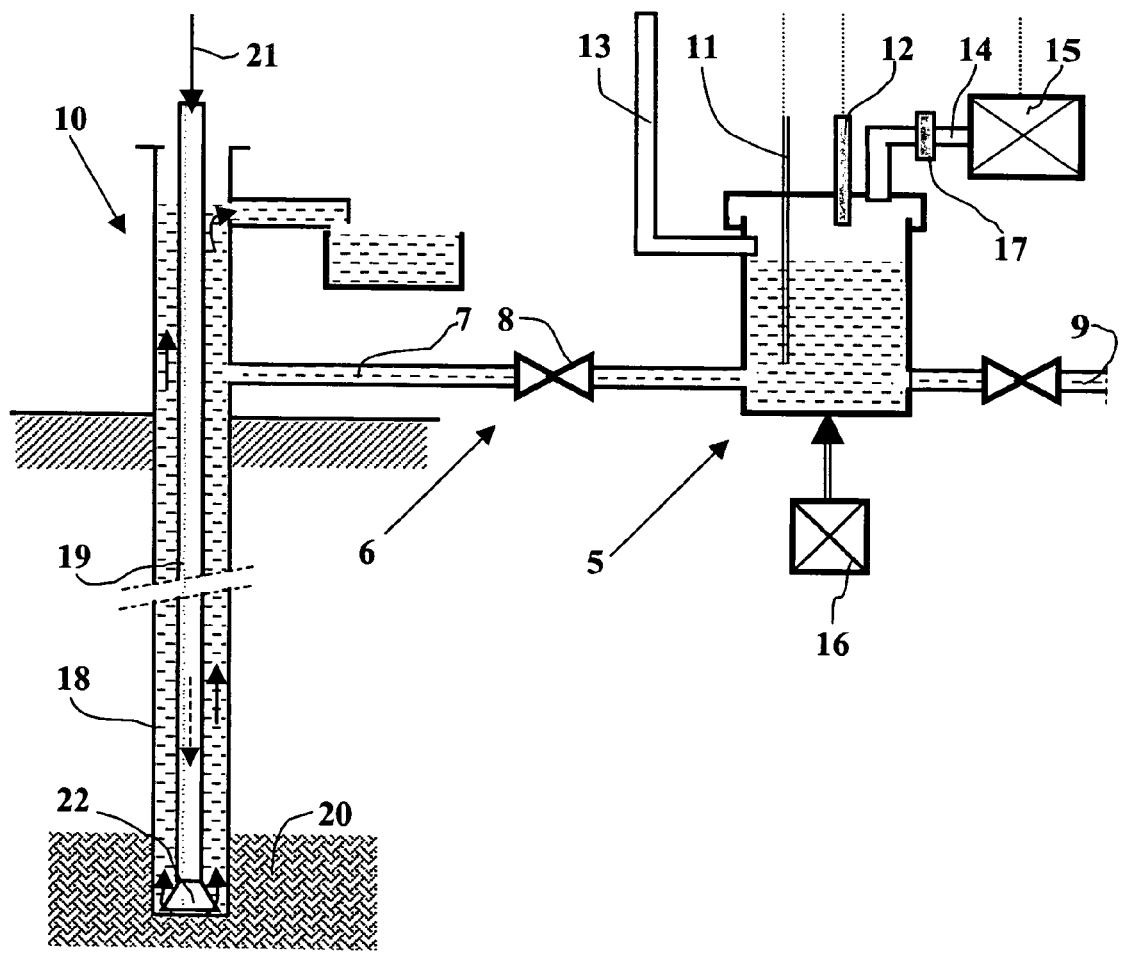
FIG. 4 illustrates one embodiment of a device according to the invention.

FIG. 4 shows schematically the principle of the measuring device. The device has a closed cell 5 connected to the wellhead 10 by sampling means 6 comprising a pipe 7 and distribution means 8, for example a pump and/or valves. Cell 5 also has means 9 for evacuating the volume of material taken from the cell. The cell has means 11 for measuring the pH, preferably continuously, and possible means 12 for measuring the pressure inside the cell. Scavenging means employing a gas, preferably an inert gas, are comprised of a pipe 13 for introducing inert gas into the cell and a pipe 14 for evacuating the gas contained in the top of the cell, above the sampled mud. The outgoing pipe 14 sends this gas to a $CO_2$ analyzer 15, for example an infrared sensor or another known measuring device. An acid pump 16 enables a strong acid to be injected into the cell at a speed and volume adjusted to the desired acidification rate and the changes in pH shown by sensor 11. Temperature control and regulation means (not shown) of the cell may complete the device.

The drilling mud can be sampled directly at the wellhead either automatically or by an operator. The sampling may be sequential, at a rate depending in particular on the drilling fluid flowrate. All the controlled sensors, analyzers, and other means are connected to a computer (not shown) that controls all these elements: valves, motors, sensors, injectors, etc.

A membrane 17 for drying the gas is placed upstream of sensor 15 to eliminate any traces of water in this top gas phase.

FIG. 1 shows schematically a geologic formation 20 partially traversed by a borehole 18 with a string 19. The drilling fluid injected at 21 raises drilling tool 22 from its position near formation 20 to the surface in the direction of the arrows.

The increased pressure in the cell can be correlated to $CO_2$ production.

EXAMPLE OF OPERATING METHOD

Automatic sampling of a given sample volume of drilling mud, at the wellhead;

Triggering of the insert gas flow to the infrared sensor;

Injection of acid by means of the syringe pump and monitoring of pH;

Continuous $CO_2$ measurement using the infrared sensor or thermal conductivity;

Measurement stopped after acidification to pH=2.

The $M_{infrared}$ measurement thus performed gives a $CO_2$ equivalent of all the species, including carbonate and hydrogen carbonate species, present in the drilling mud. From this value must be subtracted the amount $M_{density}$ of the $CO_2$ corresponding to the amount of carbonate initially present in the drilling mud, particularly due to additives added to adjust its density. This value can be determined by measuring the original formation, on-site or in the laboratory.

In the event carbonate-containing geologic formations are being drilled, geologic knowledge of the terrain gives us the proportion of carbonate in drilled area $C_{formation}$. The volume of waste contained in the drilling mud can be calculated from the volume of the hole, the mud flowrate, and the drilling rate; let V be this waste volume per liter of mud.

Hence we have the quantity of carbonate coming from the formation:

$Ca_{formation} = V_{mud} \times V \times C_{formation}$

Since $M_{formation}$ is the quantity of $CO_2$ corresponding to the quantity $Ca_{formation}$, the quantity of $CO_2$ in the geologic for mation carried by the mud from the hole bottom will be equal to:

$$M_{infrared} - M_{density} - M_{formation}$$

Thus, the method and device according to the invention gives a more accurate estimate of the quantity of $CO_2$ in place in an underground deposit, taking into account the interaction of the fluid carrying this gas, the initial conditions of the nature of this fluid, and the drilling operations in this deposit.

The invention claimed is:

1. Method for estimating the quantity of $CO_2$ present in a geologic formation comprising the following steps:
   said formation is penetrated by a well drilled from the surface,
   said formation is contacted with a drilling fluid having a pH greater than 8 that travels from the formation to the surface,
   a given quantity of return fluid is sampled at the surface and transferred to a cell,
   the pH of said quantity of fluid is measured,
   a given quantity of product acidifying said fluid is added to adjust the pH to a value of less than 4,
   the $CO_2$ level of the gas in the cell is measured after the acidification step,
   the quantity of $CO_2$ contained in the geologic formation is calculated from the $CO_2$ measurement.

2. Method according to claim 1, wherein the quantity of carbonate supplied by the geologic formation and/or by the additives in the formulation of said fluid is taken into account.

3. Method according to claim 1, wherein the pH is adjusted to approximately 2.

4. Method according to claim 1, wherein said gas is transferred from the cell to an analyzer in which the $CO_2$ level of the gas is measured by an inert gas scavenging the internal space of the cell.

5. Method according to claim 2, wherein said additives are taken into account by running the $CO_2$ measurement method on a given volume of initial fluid before contact with the formation.

6. Method according to claim 1, wherein the sampling rate is determined according to the fluid travel rate.

7. Device for estimating the quantity of $CO_2$ present in a geologic formation traversed by a well in which a drilling fluid with a pH greater than 8 travels between said formation and the wellhead at the surface, characterized in that it comprises means for sampling a given quantity of fluid at the wellhead, a cell to hold said quantity of fluid, means for measuring the pH in said cell, means for inert-gas scavenging of the internal space of the cell, means for injecting an acidifying product into said cell, and means for measuring the quantity of $CO_2$ contained in the internal space of the cell.

8. Device according to claim 7, wherein adjusting means control the acid injection means according to the pH measurement.

9. Device according to claim 7, wherein the means for measuring the quantity of $CO_2$ comprise an infrared cell or a thermal conductivity measuring cell.

10. Device according to claim 7, wherein control means carry out the following steps, at a rate determined by the fluid flowrate:
    Sampling of a quantity of fluid;
    Measurement of pH;
    Injection of a quantity of acid;
    Scavenging the cell space;
    Measurement of $CO_2$;
    Emptying the cell.

11. Device according to claim 7, including means for measuring the internal pressure of said cell.

12. Device according to claim 7, including means for regulating the temperature of said cell.

* * * * *